(12) United States Patent
Iwasaki et al.

(10) Patent No.: US 6,420,613 B1
(45) Date of Patent: Jul. 16, 2002

(54) PROCESS FOR PREPARING REDUCTANTS OF UNSATURATED ORGANIC COMPOUNDS BY THE USE OF TRICHLOROSILANE AND REDUCING AGENTS

(75) Inventors: Fumiaki Iwasaki, Tokuyama; Yoshihiro Matsumura, Fukuoka; Osamu Onomura, Nagasaki; Kenji Tanaka, Tsukuba, all of (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 09/674,960

(22) PCT Filed: Mar. 2, 2000

(86) PCT No.: PCT/JP00/01241

§ 371 (c)(1),
(2), (4) Date: Dec. 11, 2000

(87) PCT Pub. No.: WO00/53551

PCT Pub. Date: Sep. 14, 2000

(30) Foreign Application Priority Data

| Mar. 9, 1999 | (JP) | 11-61684 |
| Sep. 9, 1999 | (JP) | 11-255380 |
| Nov. 15, 1999 | (JP) | 11-323817 |

(51) Int. Cl.$^7$ ............................ C07C 37/00; C07C 37/06
(52) U.S. Cl. ........................ 568/772; 568/881; 556/413; 546/14; 546/290; 546/297; 546/298; 548/110; 548/225; 548/325.1; 548/340.1; 548/406; 564/355; 564/363; 564/415; 564/489
(58) Field of Search .................... 568/772, 881; 564/315, 363, 415, 489; 546/14, 290, 297, 298; 548/110, 225, 335.1, 340.1, 406

(56) References Cited

U.S. PATENT DOCUMENTS

| 4,536,347 A | * | 8/1985 | Horner et al. | 568/772 |
| 5,545,388 A | * | 8/1996 | Rogers et al. | 568/772 |
| 5,831,133 A | * | 11/1998 | Mimoun | 568/881 |
| 6,046,127 A | * | 4/2000 | Mimoun | 568/881 |
| 6,306,359 B1 | * | 10/2001 | Mathieu et al. | 568/881 |

OTHER PUBLICATIONS

Otter et al., "Synthesis structure and dynamics of organosilyl anilides", Organometallics, 1990, vol. 9, No. 5, p. 1557–1562.*

Boyer et al., :Enhancement of silicon–hydrogen bond reactivity in pentacoordinated structures, J. Organomet. Chem, 1986, vol. 311, No. 3, C–39–C43.*

* cited by examiner

*Primary Examiner*—Paul F. Shaver
(74) *Attorney, Agent, or Firm*—Sherman & Shalloway

(57) ABSTRACT

A method of preparing a reduced product by efficiently reducing an unsaturated organic compound by using, as a reducing agent, a trichlorosilane which is industrially cheaply available and is easy to handle, and a reducing agent therefor. A reduced product of an unsaturated organic compound is obtained by mixing the unsaturated organic compound and a trichlorosilane together to reduce the unsaturated organic compound in the presence of a compound that forms a silicon complex having five coordinations upon acting on the trichlorosilane such as an N-formylated product of a secondary amine having not less than 3 carbon atoms. The invention further provides a reducing agent comprising a particular silicon complex.

15 Claims, No Drawings

PROCESS FOR PREPARING REDUCTANTS OF UNSATURATED ORGANIC COMPOUNDS BY THE USE OF TRICHLOROSILANE AND REDUCING AGENTS

TECHNICAL FIELD

The present invention relates to a method of preparing reduced products of unsaturated organic compounds using a trichlorosilane. More specifically, the invention relates to a method of preparing reduced products by efficiently reducing unsaturated organic compounds in the presence of a particular ligand compound and, particularly, in the presence of an N-formylated product of an amine together with a trichlorosilane.

The invention further relates to a reducing agent comprising a particular silicon complex capable of efficiently reducing unsaturated organic compounds and, more particularly, to a reducing agent comprising a mononuclear or a binuclear silicon complex in which the coordination number of a silicon atom is 5 or 6.

BACKGROUND ART

The reducing reaction enables a hydrogen atom to react with an unsaturated bond only, and is a very important elementary reaction for synthesizing position-specific or stereospecific organic compounds.

In particular, secondary alcohol compounds such as 1-phenyl-1-ethanol, 2-butanol and 2-octanol are industrially important as intermediate products for dyes, perfumes and agricultural chemicals. A method of preparing the secondary alcohol compounds can be, represented by the one for reducing the ketone compounds with a reducing agent, and there have heretofore been developed many reducing agents and reducing reactions.

On the other hand, the trichlorosilane which is a very important compound as a starting material for industrially preparing highly pure polycrystalline silicon not only exhibits a reducing property but is also cheaply available and is easy to handle. In recent years, therefore, the trichlorosilane has ever been frequently used for the organic synthesis.

Under such circumstances, there has been known a method of reducing the ketone compounds to the secondary alcohol compounds by using the trichlorosilane in the presence of a dimethylformamide [Chemistry Letters, pp. 407–408, 1996].

According to the above method, however, a high yield is exhibited for the aralkyl ketone compounds but the yield is as low as 54% for the aryl ketone compounds. Therefore, the above reducing method cannot be said to be generally applicable. The reduction is not quite effected for the aliphatic ketone compounds.

It is therefore desired to develop a method of reducing unsaturated organic compounds and, particularly, reducing ketone compounds that are general applicabile by using a trichlorosilane that is cheaply available and is easy to handle.

DISCLOSURE OF THE INVENTION

In view of the above-mentioned circumstances, the present inventors have conducted a keen study and have discovered the fact that the unsaturated organic compounds are efficiently reduced when the reaction for reducing the unsaturated organic compounds is conducted by using a trichlorosilane in the presence of a particular ligand compound and, particularly, in the presence of an N-formylated product of a secondary amine having not less than 3 carbon atoms and, more particularly, in the presence of a formylated product of a cyclic amine such as pyrrolidine derivative or an N-formylated product of a secondary amine in which a carbon atom at the β-position of a nitrogen atom forms an oxo group.

That is, it is an object of the present invention to provide a method of preparing reduced products by efficiently reducing unsaturated organic compounds by using, as a reducing agent, a trichlorosilane that is industrially cheaply available and is easy to handle.

The invention further has an object of providing a reducing agent capable of efficiently reducing unsaturated organic compounds by using a trichlorosilane which is industrially cheaply available and is easy to handle.

According to the present invention, there is provided a method of preparing a reduced product of an unsaturated organic compound by mixing the unsaturated organic compound and a trichlorosilane together to reduce the unsaturated organic compound in the presence of a ligand compound which, when mixed together with the trichlorosilane, gives a signal at −15 to −120 ppm as measured by $^{29}$Si-NMR at 74.9 MHz. Here, the ligand compound stands or a compound capable of being coordinated on the trichlorosilane.

In the above-mentioned method of preparation, it is desired that:

1. The ligand compound is the one capable of giving a signal at −15 to −120 ppm as measured by $^{29}$Si-NMR at 74.9 MHz in a solution obtained by adding, into a solution of 0.2 mols of the trichlorosilane/liter, the ligand compound in an equimolar amount to the trichlorosilane and, particularly, an N-formylated product of a secondary amine having not less than 3 carbon atoms (and, particularly, a cyclic amine having not less than 3 carbon atoms or a secondary amine in which a carbon atom at the β-position of a nitrogen atom forms an oxo group); and
2. The unsaturated organic compound is at least the one selected from the group consisting of a ketone compound, an aldehyde compound and an imine compound.

According to the present invention, there is further provided a reducing agent comprising:

(a) a mononuclear silicon complex in which a silicon atom has a coordination number of 5, and among the five ligands coordinated on the silicon atom in the silicon complex, four ligands include a hydrogen atom and three chlorine atoms, and the remaining one ligand acts upon a trichlorosilane to form a stable silicon complex having five coordinations and/or, (b) a binuclear silicon complex in which each silicon atom has a coordination number of 6, and among the six ligands coordinated on each silicon atom in the silicon complex, five ligands include a hydrogen atom and four chlorine atoms, and the remaining one ligand acts upon the trichlorosilane to form a stable silicon complex having five coordinations.

In the above reducing agent, it is desired that the ligand compound capable of forming a stable silicon complex having five coordinations upon acting on the trichlorosilane is:

1. The one capable of forming a silicon complex having five coordinations that can be detected when a solution is measured by $^{29}$Si-NMR at 74.9 MHz, the solution being obtained by having the ligand compound acted on the trichlorosilane in an equimolar amount thereto in a solution of 0.2 mols of the trichlorosilane/liter;

2. The one that gives a signal at −25 to −120 ppm when a solution is measured by $^{29}$Si-NMR at 74.9 MHz, the solution being obtained by adding, to a solution of 0.2 mols of the trichlorosilane/liter, the ligand compound in an equimolar amount to the trichlorosilane; and 3. An N-formylated product of a secondary amine having not less than 3 carbon atoms (and, particularly, an N-formylated product of a cyclic amine having not less than 3 carbon atoms or an N-formylated product of a secondary amine in which a carbon atom at the β-position of a nitrogen atom forms an oxo group).

The present inventors have studied the reduction reaction conducted in the presence of a trichlorosilane having a weak reducing power and various compounds by giving attention to the fact that even the same trichlorosilane exhibits different reducing power depending upon the kind of the compound that is also made present.

As a result, the inventors have discovered the fact that the reaction for reducing the unsaturated organic compound efficiently proceeds when a particular ligand compound is made present and, particularly, when an N-formylated product of the secondary amine having not less than 3 carbon atoms is made present together with the trichlorosilane.

The mechanism for efficiently conducting the reducing reaction has not yet be en clarified: in detail, but it is presumed that the trichlorosilane having a weak reducing power is transformed into active seeds of different activities depending upon the kind of the compound that is made present in the reaction system.

Here, the N-formylated product of the secondary amine having not less than 3 carbon atoms can be represented by, for example, the following general formula (I),

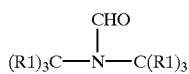

(I)

wherein R1 may be the same or different, and are hydrogen atoms or monovalent organic groups, and at least one of R1 is an organic group.

The inventors have further speculated that the active seeds may comprise a silicon complex derived from the trichlorosilane, and have forwarded the study relying upon the $^{29}$Si-NMR measurement to specify the active seed that exhibits a high activity of reaction.

First, a solution of 0.2 mols of trichlorosilane/liter was prepared by using a dichloromethane as a solvent, and to which was added a dimethylformamide in an equimolar amount to the trichlorosilane. The mixture solution was measured by $^{29}$Si-NMR at 74.9 MHz to detect only two signals at −186.4 ppm and −192.0 ppm indicating the formation of a silicon complex having six coordinations in which the dimethylformamide is coordinated on the trichlorosilane.

It is a known fact that the silicon atom usually forms structures of not only a valence of 4 but also of higher valences, and further forms not only a complex having six coordinations but also a complex having five coordinations. The inventors, therefore, have paid attention to the above fact, speculated that active seeds other than the complex having six coordinations may be exhibited by the pyrrolidine derivatives which, when the trichlorosilane is made present, exhibit activities higher than when the dimethylformamide is made present, and have taken the NMR measurement under the same conditions.

As a result, it was clarified that the silicon complex does not form a complete complex of six coordinations with the equimolar amount of trichlorosilane like the dimethylformamide, but exists as a mixture of the complex having five coordinations and the complex having six coordinations, or as a mixture of the trichlorosilane and the complex having five coordinations.

Complexes obtained by coordinating various compounds on the trichlorosilane were studied concerning a relationship between the number of coordinations of the silicon atom and the activity (reducing power), to find the fact that a higher activity is exhibited when a ligand compound is coordinated to form a complex having five coordinations than when a ligand compound is coordinated which, when coordinated on the trichlorosilane, is capable of forming a silicon complex having six coordinations only. That is, the present inventors have also discovered means for controlling the reducing power of the reducing agent by using the trichlorosilane.

Here, a stable silicon complex having five coordinations is the one that can be detected when a solution is measured by $^{29}$Si-NMR at 74.9 MHz, the solution being obtained by having a ligand compound acted in an equimolar amount on the trichlorosilane in, for example, a solution of 0.2 mols of the triclorosilane/liter.

In the NMR measurement, detection of the silicon complex having five coordinations is confirmed by observing a signal at 15 to −120 ppm. It can, therefore, be said that a novel condensing agent of the present invention comprises a silicon complex obtained by mixing, in a solvent, a trichlorosilane and!a compound that exhibits a signal at −15 to −120 ppm when a solution thereof is measured by the $^{29}$Si-NMR at 74.9 MHz, the solution being obtained by adding, into a solution of 0.2 mols of the trichlorosilane/ litter, a ligand compound in an equimolar amount to the trichlorosilane.

As the ligand compound that gives such a stable silicon complex having five coordinations, there can be exemplified an N-formylated product of a secondary amine having not less than 3 carbon atoms (particularly, a formylated product of a cyclic amine having not less than 3 carbon atoms, or an N-formylated product of a secondary amine in which a carbon atom at the β-position of a nitrogen atom forms an oxo group.

BEST MODE FOR CARRYING OUT THE INVENTION

In the preparation method of the present invention, an unsaturated organic compound is reduced by using a trichlorosilane in the presence of a ligand compound which, when mixed with the trichlorosilane, gives a signal at −15 to −120 ppm as measured by $^{29}$Si-NMR at 74.9 MHz and, particularly, in the presence of an N-formylated product of a secondary amine having not less than 3 carbon atoms.

<Unsaturated Organic Compounds>

Any unsaturated organic compound can be used without limitation provided it can be used for the reduction reaction as a starting material or as an intermediate product for the organic synthesis. Usually, there can be exemplified carbonyl compounds (particularly, ketone compounds and aldehyde compounds) and imine compounds as unsaturated organic compounds of which the products after reduction are useful for the organic synthesis.

That is, in the above reducing reaction, a hydrogen atom is added to the unsaturated bond of the unsaturated organic compound that its a starting material to obtain the following products.

| Starting material | Product |
|---|---|
| ketone compound <br> $\diagup$C(=O) | secondary alcohol <br> $\diagup$CH(OH) |
| aldehyde compound <br> —CH=O | primary alcohol <br> —CH$_2$OH |
| imine compound <br> $\diagup$C=N— | secondary amine <br> $\diagup$CH—NH— |

Carbonyl Compounds:

When the starting material used in the reducing reaction is a carbonyl compound, there can be used, without limitation, any aldehyde compound or any ketone compound that is easily available as a reagent or an industrial starting material depending upon the kind of the desired primary alcohol compound or the secondary alcohol compound.

Concrete examples of the compounds are described below. As the aldehyde compound, there can be exemplified aliphatic chain aldehyde compounds having 2 to 20 carbon atoms, such as acetaldehyde, propanal, butanal, pentanal, hexanal, heptanal, octanal, nonanal and decanal; arylaldehyde compounds having 5 to 10 carbon atoms, such as benzaldehyde, 2-chlorobenzaldehyde, 4-chlorobenzaldehyde, 2-nitrobenzaldehyde, 4-nitrobenzaldehyde, 4-hydroxybenzaldehyde, 4-acetoxybenzaldehyde, 2-furaldehyde, 2-thiophenecarboxyaldehyde, and 3-thiophenecarboxyaldehyde; aralkylaldehyde compounds having 7 to 13 carbon atoms, such as phenylacetaldehyde, etc.; and α, β-unsaturated aldehyde compounds having 3 to 15 carbon atoms, such as acrolein, trans-2-pentenal, trans-2-hexenal, and trans-2-heptenal. As the ketone compounds, there can be exemplified aliphatic chain ketone compounds having 3 to 20 carbon atoms, such as acetone, 2-butanone, 2-heptanone, 3-pentanone, 4-methyl-2-pentanone, 2-hexanone, 3-hexanone, 2-heptanone, 3-heptanone, 4-heptanone, 2-octanone, 3-octanone, 2-nonanone, 3-nonanone, 5-nonanone, 2-decanone, 3-decanone, 4-decanone , 2-undecanone, and 6-undecanone; alicyclic ketone compounds having 3 to 20 carbon atoms, such as cyclopropanone, cyclobutanoe, cyclopentanone, cyclohexanone, cycloheptanone, cyclooctanone, cyclononanone, cyclodecanone, 4-tert-butylcyclohexanone and 2-methylcyclohexanone; aryl ketone compounds such as acetophenone, benzophenone, 9-acetylanthracene, 2-acetylbiphenylene, 4-acetylbiphenyl, acetylpyrazine, 2-acetylpyridine, 3-acetyl-2,4-dimethylfuran, 3-acetyl-2,4-dimethylpyrrole, 5-acetyl-2,4-dimethyithiazole, 3-acetyl-2,5-dimethylthiophene, 2-acetylfluorene, 2-acetylfuran, 3-acetylindole, 2-acetyl-5-methylfuran, 2-acetyl-3-methylthiophene, 2-acetylnaphthalene, 2-acetylphenanthrene, 3-acetylphenanthrene, 9-acethylphenanthrene, 2-acetylthiazole and 2-acethylthiophene; aralkyl ketone compounds such as 2-phenylcyclohexanone, 4-phenylcyclohexanone, 1-phenyl-2-butanone, 4-phenyl-2-butanone, 2-phenylcyclopentanone, 2-phenylcycloheptanone, 3-phenyl-1-indanone, 4-acetyl-1-methylcyclohexene, and 2-acetyl-5-norbornene; and α,β-unsaturated ketone compounds having 4 to 10 carbon atoms, such as 3-butene-2-on, 1-pentene-3-on, 3-pentene-2-on, 4-hexene-3-on, 2-cyclopentene-1-on, 3-methyl-2-cyclopentene-1-on, 2-cyclohexene-1-on, and 2-cycloheptene-1-on.

Among these compounds, there can be preferably used, from the standpoint of expecting particularly high yields, ketone compounds and α,β-unsaturated ketone compounds having 4 to 10 carbon atoms selected from aliphatic chain aldehyde compounds having 2 to 20 carbon atoms, arylaldehyde compounds having 5 to 10 carbon atoms, aralkylaldehyde compounds having 7 to 13 carbon atoms, α,β-unsaturated aldehyde compound having 3 to 15 carbon atoms, aliphatic chain ketone compounds having 3 to 20 carbon atoms, alicyclic ketone compounds having 3 to 20 carbon atoms and aralkyl ketone compounds.

On the other hand, very small kinds of imine compounds have been placed in the market industrially or as reagents. Usually therefore, the imine compound that corresponds to a desired amine compound is prepared by reacting the above carbonyl compound with ammonia or with a primary amine compound. Examples of the primary amine compound that is used for the synthesis of the imine compound include aliphatic amine compounds having 1 to 10 carbon atoms, such as methylamine, 2-ethylamine, 1-propylamine, 2-propylamine, 1-butylamine, 2-butylamine, 1-pentylamine, cyclopentylamine, 1-hexylamine and cyclohexylamine; and aromatic amine compounds having 3 to 10 carbon atoms, such as aniline, 2-aminothiazole, benzylamine, diphenylmethylamine, 1-naphthylainine and 2-naphthylamine.

The imine compound used in the present invention is synthesized by heating the above-mentioned carbonyl compound, ammonia and the primary amine compound in an inert organic solvent such as benzene, xylene or diethyl ether in the presence of an acidic catalyst such as p-toluenesulfonic acid.

Concrete examples of the imine compound include aliphatic imine compounds having 2 to 20 carbon atoms, such as ethylideneimine, propylideneimine, butylideneimine, pentylideneimine, hexylideneimine, N-ethylidenemethylamine, N-propylidenemethylamine, N-butylidenemethylamine, N-pentylidenemethylamine, N-hexylidenemethylamine, N-ethylidenemethylamine, N-ethylidene-1-butylamine, N-ethylidene-1-pentylamine, N-ethylidene-1-hexylamine, N-methylidenecyclohexylamine, N-ethylidenecyclohexylamine, N-butylidenecyclohexylamine, N-isopropylidenemethylamine, N-isopropylidenemethylamine, N-isopropylidenemethylamine and N-isopropylidenecyclohexylamine; and aromatic imine compounds having 7 to 20 carbon atoms, such as N-benzylideneamine, N-benzylidinemethylamine, N-benzylidinemethylamine, N-benzylidene-1-propylamine, N-benzylidene-1-butylamine, N-benzylideneaniline, 1-methylimino-1-phenylethane, 1-ethylimino-1-phenylethane, 1-propylimino-1-phenylethane, 1-cyclohexylimino-2-phenylethane, 1-phenylimino-1-phenylethane, 1-benzylimino-1-phenylethane, N-diphenylmethylidenemethylamine, N-diphenylmethylideneethylamine and N-diphenylmethylidenepropylamine.

Among these compounds, it is desired, from the standpoint of expecting particularly high yields, to use those imine compounds selected from the aromatic imine compounds having 7 to 20 carbon atoms.

These imine compounds include isomers of syn-modifications and anti-modifications depending upon the kinds of compounds. In the present: invention, all of these isomers can be used without any distinction.

<Reaction Reagents>

Trichlorosilane:

As the trichlorosilane used in the reducing method of the present invention, there can be used, without lamination, those that have been placed in the market as reagents or industrial starting materials. The trichlorosilane is generally used as a starting material of highly pure silicon and has, hence, been placed in the market in a very highly pure form, and can be used without refining it.

The reaction of the unsaturated organic compound with the trichlorosilane according to the present invention is a stoichiometric reaction. Therefore, there is no particular limitation on the amount of the trichlorosilane provided it is used in an amount of not less than a mole per mole of the unsaturated organic compound. When the amount is too large, however, a cumbersome operation is required for removing silica that is by-produced in the neutralizing step which is an after-treatment. Usually, therefore, the trichlorosilane is used in an amount of from 1 to 5 moles and, preferably, from 1 to 3 moles per a mole of the unsaturated organic compound. Ligand compound:

In the present invention, the unsaturated organic compound is reduced by using a ligand compound which, when mixed with the trichlorosilane, gives a signal at −15 to 120 ppm as measured by $^{29}$Si-NMR at 174.9 MHz and, particularly, by using the trichlorosilane in the presence of a formylated product of a secondary amine having not less than 3 carbon atoms.

In the reducing reaction, the reaction activating seed corresponds to −15 to −120 ppm in terms of a chemical shift value of $^{29}$Si-nuclear magnetic resonance (NMR) spectrum. For this purpose, therefore, it is necessary to make present a ligand compound that gives a signal of a chemical shift value within this range.

The N-formylated products of the secondary, amine having not less than 3 carbon atoms can be represented by, for example, the general formula (I),

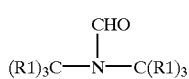

(I)

wherein R1 may be the same or different, and are hydrogen atoms or monovalent organic groups, and at least one of R1 is an organic group.

Among the formylated products the general formula (I), it is desired to use a formylated product of a cyclic amine having not less than 3 carbon atoms and/or an N-formylated product of a secondary amine in which a carbon atom at the β-position of a nitrogen atom forms an oxo group.

Concrete examples of the formylated product of the cyclic amine having not less than 3 carbon atoms include those represented by the following general formula (II),

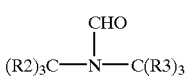

(II)

wherein R2 and R3 may be the same or different, and are hydrogen atoms or monovalent organic groups, and at least a set of R2 and R3 may be bonded together to form a ring having not less than 3 carbon atoms, and examples of the N-formylated products of the secondary amine in which a carbon atom at the β-position of a nitrogen atom forms an oxo group include those represented by the following general formula (III),

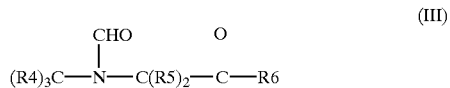

(III)

wherein R4 and R5 may be the same or different, and are hydrogen atoms or monovalent organic groups, R4 and R5 may be bonded together to form a ring, and R6 is an amino group, an alkoxyl group, an alkylthio group, an aromatic hydrocarbon group or an aliphatic hydrocarbon group that may have a substituent.

Concrete examples of these compounds are as described below. Namely, the formylated products of the cyclic amine include formylated products of cyclic amines without having substituent on the ring, such as 1-formylpyrrolidine, 1-formylpiperildine, 1-formylhexamethyleneimine, 1-formylheptamethyleneimine, 1-formylpyrrole, 1-formylimidazole, and 1-formylpyrrazole; prolinol derivatives such as 1-formyl-2-hydroxymethylpyrrolidine, 1-formyl-2-benzyloxymethylpyrrolidine, and 1-formyl-2-diphenylhydroxymethylpyrrolidine; and oxazoline compounds such as 3-formyl-4-(S)-isopropyloxazoline, 3-formyl-4-(S)-phenyloxazoline, and 3-formyl-4-(S)-phenylaminocarbonyloxazoline.

Among them, it is desired, from the standpoint of expecting high yields to use formylated products of cyclic amine without substituent on the ring, such as 1-formylpyrrolidine, 1-formylpiperidine, 1-formylhexamethyleneimine and 1-formylheptamethyleneimine; prolinol derivatives such as 1-formyl-2-hydroxymethylpyrrolidine; and oxazoline compounds such as 3-formyl-4-(S)-phenylaminocarbonyloxazoline.

As the N-formylated products of secondary amine in which a carbon atom at the β-position of a nitrogen atom forms an oxo group, there can be exemplified prolineamide derivatives such as N-phenyl-1-formylprolineamide, N-benzyl-1-formylprolineamide, N-hexyl-1-formylprolineamide, N-diphenyl-1-formylprolineamide, N,N-diphenylmethyl-1-formylprolineamide, N-(1-naphthyl)-1-formylprolineamide, and N-tert-butyl-1-formylprolineamide; proline ester derivatives such as 1-formylprolinebenzyl ester, 1-formylproline-tert-butyl ester, 1-formylprolinehexyl ester, 1-formylprolinephenyl ester, 1-formylprolinemethyl ester, and 1-formylprolinethyl ester; peptide compounds such as N-formyl-L-prolyl-L-phenylalaninemethyl ester, and N-formyl-L-prolyl-D-phenylalaninemethyl ester; and N-formyl-N-methylglycinebenzyl ester.

Among them, it is desired, from the standpoint of expecting high yields, to use prolineamide derivatives such as N-phenyl-1-formylprolineamide, N-benzyl-1-formylprolineamide, N-hexyl-1-formylprolineamide, N-diphenylmethyl-1-formylprolineamide, N-(1-naphtyl)-1-formylprolineamide, and N-tert-butyl-1-formylprolineamide; proline ester derivatives such as 1-formylprolinebenzyl ester, 1-formylproline-tert-butyl ester, 1-formylprolinehexyl ester, 1-formylprolinephenyl ester, and 1-formylprolinethyl ester; peptide compounds such as N-formyl-L-prolyl-L-phenylalaninemethyl ester, and N-formyl-L-prolyl-D-phenylalaninemethyl ester; and N-formyl-N-methylglycinebenzyl ester.

Many of the above-mentioned form 1 compounds are placed in the market as reagents and are easily available, but can be easily synthesized by, for example, a method described below.

That is, the formylated product of a cyclic amine without substituent on the ring can be synthesized by reacting a cyclic amine which is easily available as an industrial starting material or as a reagent with a formylating agent such as a mixed acid anhydride comprising methyl formate, ethyl formate or formic acid and acetic acid. Further, the prolineamide derivatives can be synthesized by preparing an acid chloride from a proline and a thionyl chloride, followed by the reaction with a predetermined amine compound to form an amide product of which nitrogen atoms are then formylated with the formylating agent. The proline ester derivatives can be synthesized by similarly reacting an acid chloride with a predetermined alcohol compound to form an ester product which is, then, formylated with the, formylating agent. The prolinol derivatives can be synthesized by reducing the proline ester obtained by the above method with a sodium boron hydride and, as required, etherifying the hydroxyl group to effect the formylation with a formylating agent, or by reacting a prolinemethyl ester with an excess of Grignard reagent. Further, the N-formyl-N-methylglycinebenzyl ester can be synthesized by benzyl-esterifying an N-methylglycine which is easily available, followed by the formylation.

Further, the oxazoline derivatives can be synthesized by reducing an amino acid methyl ester to transform it into an amino alcohol, followed by the cyclization and formylation.

Among the above-mentioned formylated products, the compounds derived from prolinol, prolineamide or proline ester have an asymmetric carbon atom at the second position of the pyrrolidine ring and, hence, there exist isomers of the S-modification and R-modification. In the present invention, however, the isomers of either modification can be used without any problem and, besides, the isomers of racemic modification can be also used.

Among the above-mentioned formylated products, the compounds derived from the amino acid have an asymmetric carbon atom at the α-position of the nitrogen atom and, hence, there exist isomers of the S-modification and R-modification. In the present invention, however, the isomers of either modification can be used without any problem and, besides, the isomers of racemic modification can be also used.

In the present invention, when an optically pure isomer of a compound derived from prolinol, prolineamide or proline ester is used, the reduced product such as a secondary alcohol compound or a secondary amine compound may often exhibit optical activity. Though not yet satisfactory from the standpoint of optical purity, the optical activity is exhibited for the first time by the secondary alcohol compound or by the secondary amine compound which is the product in reducing the ketone compound or the imine compound with the trichlorosilane according to the present invention.

There is no particular limitation on the amount of using the formylated compound in the present invention. When the amount is too small, however, the reaction rate becomes very small and when the amount is too great, cumbersome removal operation is required in the after-treatment giving disadvantage in economy. It is, therefore, desired that the formylated compound is used in an amount of from 0.01 to 3 mols and, preferably, from 0.05 to 2 mols per mole of the unsaturated organic compound.

Organic Solvents:

The present invention is usually conducted in an organic solvent. Any organic solvent can be used in the present invention without limitation provided it does not impair the reducing reaction. Concrete examples of the organic solvent include halogenated aliphatic hydrocarbons such as methylene chloride, chloroform and carbon tetrachloride; ethers such as tetrahydrofurane, diethyl ether, isopropyl ether and 1,4-dioxane; esters such as ethyl acetate, propyl acetate and butyl acetate, nitriles such as acetonitrile and propionitrile; aromatic hydrocarbons such as benzene, xylene and toluene; aliphatic hydrocarbons such as hexane and heptane; carbonates such as dimethyl carbonate and chlorobenzene; and halogenated aromatic hydrocarbons such as chlorobenzene.

Among them, it is desired to use, from the standpoint of expecting particularly high yields, halogenated aliphatic hydrocarbons, ethers, esters, aromatic hydrocarbons and carbonates.

In the present invention, water acts as a reaction-impairing factor. It is therefore desired to use the solvent in a dry form. An optimum method of drying the solvent may differ depending upon the solvent and cannot be exclusively stated. However, the dry solvent can be prepared by bringing the solvent into contact with a dehydrating agent such as calcium chloride, zeolite or magnesium sulfate or with a hydride such as calcium hydride, followed by distillation.

There is no particular limitation on the amount of the organic solvent. When the amount is too large, however, the yield becomes small per a batch, which is not economical. When the amount is too great, on the other hand, stirring is impaired. It is therefore desired to use the organic solvent in such an amount that the concentration of the unsaturated organic compound is from 0.1 to 60% by weight and, preferably, from 1 to 50% by weight.

Silicon Complexes:

The reducing agent of the present invention comprises a mononuclear or binuclear silicon complex having particular ligands and having a number of coordinations of a silicon atom of 5 or 6. In the mononuclear or binuclear silicon complex, among 5 or 6 ligands coordinated on the silicon atom, four ligands include one hydrogen atom and three chlorine atoms, and at least one of the remaining one or two ligands is a ligand compound (hereinafter also referred to as particular ligand compound) which acts upon the trichlorosilane to form a stable silicon complex having five coordinations.

There is no particular limitation on the structure of the silicon complex which is the reducing agent of the present invention provided the above-mentioned conditions are satisfied. Concrete structure of the representative silicon complex is as described in (1) or (2) below.

(1) A mononuclear silicon complex having five coordinations in which one hydrogen atom, three chlorine atoms and one particular ligand compounds are coordinated on a silicon atom. The silicon complex has the structures represented by the following general formulas (wherein L is a particular ligand compound) in which one particular ligand compound is coordinated on a trichlorosilane molecule.

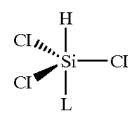

[A]

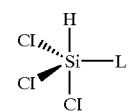

[B]

-continued

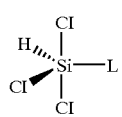

(2) A binuclear complex of silicon having two silicon atoms, or a silicon complex having 6 ligands wherein one hydrogen atom, four chlorine atoms (in which two chlorine atoms are bidentate ligands coordinated on two silicon atoms) and one particular ligand compound are coordinated on each silicon atom. The silicon complex is a binuclear complex of silicon in which two particular ligand compounds act upon the two trichlorosilane molecules, and has the structures represented by the following general formulas (wherein L1 and L2 are particular ligand compounds which may be different from each other).

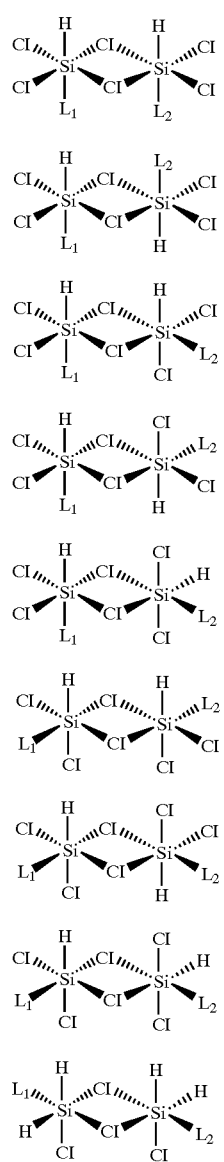

Among the above silicon complexes, it is desired to use the silicon complexes of (1) above from the standpoint of a high reducing power.

There is no particular limitation on the particular ligand compound in the silicon complex which is a reducing agent of the present invention provided it is a ligand capable of acting upon the trichlorosilane to form a stable silicon complex having five coordinations. Here, the stable silicon complex having five coordinations stands for a silicon complex which is so stable that its presence can be confirmed by any method. From the standpoint of reducing power, however, it is preferably such a complex that when the particular ligand compound is added to a solution of 0.2 mols of trichlorosilane/liter in an equimolar amount to the trichlorosilane, a signal (due to a silicon atom having five coordinations) is observed at −15 to −120 ppm as measured by $^{29}$Si-NMR at 74.9 MHz.

The $^{29}$Si-NMR measurement is taken by adding a particular ligand compound to a solution of a trichlorosilane of a concentration of 0.2 mols/liter, the particular ligand compound being added in a mole number equal to the mole number of the trichlorosilane to prepare a sample, introducing the sample into a glass sample tube, and taking a measurement over a temperature range of from −50 to 50° C. by using the tetramethylsilane (TMS) as a standard substance. When the particular ligand compound and the trichlorosilane are made present in a solution, in general, a complex is formed, and there exists an equilibrium relationship between the trichlorosilane and the ligand compound, i.e., between the trichlorosilane and the complex having five coordinations or between the complex having five coordinations and the complex having six coordinations depending upon the kind of the ligand compound. When the presence of the complex having five coordinations is to be measured, therefore, it is considered that there may exist an optimum mixing ratio between the trichlorosilane and the ligand compound. A reducing agent having a high reducing power is obtained when use is made, as the particular ligand compound, of a ligand compound from which the complex having five ligands can be detected when measured by $^{29}$Si-NMR under the above-mentioned conditions.

As the optimum compound that could become as the above particular ligand compound, there can be exemplified organic compounds including a nitrogen atom and, particularly, the above-mentioned N-formylated product (particularly, an N-formylated product of a cyclic amine having not less than 3 carbon atoms or an N-formylated product of a secondary amine in which a carbon atom at the β-position of the nitrogen atom forms an oxo group).

The reducing agent of the present invention can be obtained by mixing a compound serving as the particular ligand compound and the above-mentioned trichlorosilane in a solvent.

There is no particular limitation on the solvent that is used, and the above-mentioned organic solvent can be used provided it is not reduced with the reducing agent of the present invention. There can be particularly preferably used halogenated aliphatic hydrocarbons or aromatic hydrocarbons since they act little upon the trichlorosilane and form a silicon complex having a strong reducing power. As described above, further, it is desired to use the organic solvent which has been dried in advance.

The thus obtained reducing agent of the present invention exhibits a very strong reducing power and effectively acts upon the reaction for reducing unsaturated organic compounds such as ketone compounds that could not be reduced so far with the trichlorosilane only. When the reducing agent of the invention is used for the reducing reaction (hereinafter, the reaction of this case is called main reducing reaction), the trichlorosilane and the compound that serves as a particular ligand may be mixed in advance in a solvent, or the trichlorosilane and the compound that serves as the particular ligand may be added to the reaction system.

In the main reducing reaction, a group >C=O of the ketone compound is transformed into a group >CH—OH— being reduced by the action of a hydrogen atom Si—H coordinated on the silicon atom of the silicon complex which is a reducing agent of the present invention. The silicon complex which is the reducing agent of the present invention is obtained by making present the trichlorosilane and the compound that serves as a particular ligand in the solution. Here, as described above, there exists an equilibrium relationship between the trichlorosilane and the complex having five coordinations, or between the complex having five coordinations and the complex having six coordinations. In conducting the reducing reaction, therefore, when the trichlorosilane is made present in an excess amount, the compound that serves as the particular ligand reproduced from the reducing agent that is used is coordinated on the trichlorosilane, thereby to reproduce a new reducing agent in the reaction system. Therefore, the reducing agent of the present invention needs not necessarily be made present in an equimolar amount to the starting ketone compound in the reaction system reckoned as Si—H. It is therefore realistic to consider that the amount of the reducing agent of the present invention in the main reducing reaction is the amount of the trichrolosilane and of the compound that serves as the particular ligand.

In using the reducing agent comprising the silicon complex, the amounts of the trichlorosilane and of the particular ligand compound are basically the same as the above-mentioned amounts of the trichlorosilane and the N-formylated product. Concretely speaking, there is no particular limitation on the amount of the trichlorosilane provided it is used in an amount of not smaller than one mole per mole of the unsaturated organic compound. When the amount is too large, however, a cumbersome operation is required for removing silica that is by-produced in the neutralizing step which is the after-treatment. Usually, therefore, the trichlorosilane is used in an amount of from 1 to 5 moles and, preferably, from 1 to 3 moles per mole of the unsaturated organic compound. The amount of the compound that serves as a particular ligand varies depending upon the kind of the compound and cannot be exclusively specified. When the amount is too small, however, the rate of reducing reaction becomes very low and when the amount is too large, on the other hand, a cumbersome operation is required for removal from the product, which is disadvantageous in economy, too. Usually, therefore, the compound that serves as the particular ligand is used in an amount of from 0.01 to 3 moles and, particularly, from 0.05 to 2 moles per mole of the unsaturated organic compound.

The reducing reaction is conducted by using the reducing agent usually in an organic solvent. As the organic solvent, there can be used without limitation the above-mentioned organic solvent used for preparing the reducing agent of the present invention. There is no particular limitation on the amount of the organic solvent used for the main reducing reaction. When the amount is too large, however, the yield per a batch becomes small, which is not economical. When the amount is too large, on the other hand, the stirring is impaired. Usually, therefore, it is desired to use the organic solvent in such an amount that the concentration of the unsaturated organic compound is from 0.1 to 60% by weight and, preferably, from 1 to 50% by weight.

<Reaction Conditions>

There is no particular limitation on the operation procedure for conducting the preparation method of the present invention. The method, however, is conducted by adding, into the reaction container, an unsaturated organic compound, a particular ligand compound such as N-formylated product and an organic solvent, followed by the addition of the trichlorosilane at a predetermined temperature.

There is no particular limitation on the reaction temperature of the present invention. When the temperature is too, high, however, the side-reaction is promoted and when the temperature is too low, the rate of reaction becomes very small. Usually, therefore, the temperature is selected to be from −78 to 50° C. and, preferably, from −30 to 40° C.

The reaction time according to the present invention varies depending upon the kind of the unsaturated organic compound that is used and cannot be exclusively specified. Usually, however, the reaction time of from 1 to 30 hours is sufficient.

The present invention can be conducted under any one of a normal pressure condition, a reduced pressure condition or an elevated pressure condition. Further, since water acts as a reaction-impairing factor, the present invention is desirably conducted in an inert gas atmosphere such as of nitrogen, helium or argon, or in a dry air atmosphere.

There is no particular limitation on the method of isolating and refining the thus obtained reduced product, and any known method can be employed. For example, an aqueous solution of sodium carbonate is added to the reaction solution to completely neutralize the reaction system, and the product is extracted by adding an organic solvent which is not compatible with water. The obtained organic solvent is dried, the solvent is distilled off under reduced pressure, and the residue is isolated and refined through a silica gel column chromatography.

EXAMPLES

The invention will now be concretely described by way of Working Examples to which only, however, the invention is in no way limited.

The formylated products of cyclic amines and formylated products of secondary amines in which a carbon atom at the β-position of a nitrogen atom forms an oxo group (hereinafter also referred to as formamide compounds) used in Examples, were prepared by a method described below.

That is, a formylated product of a cyclic amine without substituent on the ring was prepared by reacting a cyclic amine with a methyl formate. The prolineamide derivative was prepared in a manner that an acid chloride was prepared by reacting a proline with a thionyl chloride, and was reacted with a predetermined amine so as to be transformed into a prolineamide derivative, followed by the reaction with a methyl formate. The proline ester derivative was prepared in a manner that the above acid chloride was reacted with a predetermined alcohol so as to be transformed into a proline ester derivative, followed by a methyl formate.

The prolinol derivative was prepared in a manner that the above proline ester derivative was transformed with a sodium borohydride into a prolinol derivative, followed by the reaction with a methyl formate. As required, further, the prolinol derivative was etherified for its hydroxyl group with a benzyl chloride. Moreover, the proline ester derivative was prepared by being reacted with an excess of a phenylinagnesium bromide.

Further, the N-formyl-N-methylglycine ester was synthesized by esterifying the N-methylglycine by the same method as the one described above, followed by the formylation with the methyl formate.

Example 1

Into a 30-ml eggplant-type flask, there were added 0.120 g (1 mmol) of an acetophenone (reagent of the special grade manufactured by Wako Junyaku Co.) as a ketone compound, 0.150 g (1.5 mmols) of a 1-formylpyrrolidine as a formylated product of a cyclic amine, and 5 ml of a methylene chloride (reagent of the special grade manufactured by Wako Junyaku Co.) as a solvent, which were, then, cooled down to 0° C. in a nitrogen atmosphere. Into the solution was dropwisely added a methylene chloride solution containing 0.203 g (1.5 mmols) of a trichlorosilane (manufactured by Shin-etsu Kagaku Co.) to conduct the reaction for 12 hours.

After the reaction, the reaction solution was poured into 50 ml of a saturated aqueous solution of sodium carbonate, and the extraction operation was effected three times with 30 ml of the methylene chloride. The obtained solution of methylene chloride was dried on magnesium sulfate, condensed, and the residue was isolated and refined through a silica gel column chromatography to obtain 0.110 g of a 1-phenyl-1-ethanol (yield, 90%).

Examples 2 to 6

The operation was conducted in the same manner as in Example 1 but using the formamide compounds shown in Table 1 as solvents instead of the 1-formylpyrrolidine. The results were as shown in Table 1. The formylamide compounds used here were all formylated products of cyclic amines.

TABLE 1

| Ex. No. | Formamide compound | Solvent | Yield (%) |
|---|---|---|---|
| 2 | 1-formylpiperidine | methylene chloride | 72 |
| 3 | 1-formylhexamethyleneimine | methylene chloride | 78 |
| 4 | 1-formylheptamethyleneimine | methylene chloride | 77 |
| 5 | 1-formylpyrrolidine | tetrahydrofuran | 84 |
| 6 | 1-formylpyrrolidine | chloroform | 86 |

Example 7

The operation was conducted in the same manner as in Example 1 but using an N-phenyl-1-formyl-(S)-prolineamide which was an amide compound having an oxo group on a carbon atom at the β-position of the nitrogen atom, as a formamide compound, instead of using the 1-formylpyrrolidine and conducting the reaction for 15 hours. As a result, there was obtained 0.121 g of a 1-phenyl-1-ethanol (yield, 99%). Further, this compound was measured for its optical purity to be 32.5% ee (R).

Examples 8 to 21

The operation was conducted in the same manner as in Example 1 but using formamide compounds shown in Table 2 instead of using the 1-formylpyrrolidine and conducting the reaction for 15 hours. The results were as shown in Table 2. Examples 8 to 10 were the cases where different kinds of formylated products of cyclic amines were used as the formamide compounds, and Examples 11 to 21 were the cases where different kinds of amide compounds having an oxo group on a carbon atom at the β-position of the nitrogen atom were used as the formamide compounds.

TABLE 2

| Ex. No. | Formamide compound | Yield (%) | Optical Purity R (% ee) |
|---|---|---|---|
| 8 | 1-formyl-(S)-2-hydroxymethylpyrrolidine | 98 | 8.7 |
| 9 | 1-formyl-(S)-2-benzyloxymethylpyrrolidine | 76 | 14.2 |
| 10 | 1-formyl-(S)-2-diphenylhydroxymethylpyrrolidine | 72 | 10.5 |
| 11 | N-benzyl-1-formyl(S)-prolineamide | 77 | 25.0 |
| 12 | N-benzyl-1-formyl(S)-prolineamide | 90 | 21.0 |
| 13 | N-diphenylmethyl-1-formyl-(S)-prolineamide | 94 | 21.8 |
| 14 | N-(1-naphthyl)-1-formyl-(S)-prolineamide | 95 | 44.0 |
| 15 | N-tert-butyl-1-formyl-(S)-prolineamide | 87 | 22.5 |
| 16 | 1-formyl-(S)-prolinebenzyl ester | 96 | 22.0 |
| 17 | 1-formyl-(S)-proline-tert-butyl ester | 94 | 12.7 |
| 18 | 1-formyl-(S)-prolinehexyl ester | 71 | 18.3 |
| 19 | 1-formyl-(S)-prolinephenyl ester | 98 | 9.6 |
| 20 | 1-formyl-(S)-prolineethyl ester | 90 | 19.1 |
| 21 | 1-formyl-1-methylglycinebenzyl ester | 88 | — |

Example 22

The operation was conducted in the same manner as in Example 1 but using the 1-formylpyrrolidine in an amount of 0.1 mmol and conducting the reaction for 24 hours to obtain 0.072 g of a 1-phenyl-1-ethanol (yield, 59%).

Examples 23 to 34

The operation was carried out in the same manner as in Example 1 but using 0.1 mmol of formamide compounds shown in Table 3 and conducting the reaction for 24 hours. The results were as shown in Table 3.

TABLE 3

| Ex. No. | Formamide compound | Yield (%) | Optical Purity R (% ee) |
|---|---|---|---|
| 23 | 1-formyl-(S)-2-hydroxymethylpyrrolidine | 61 | 6.4 |
| 24 | N-phenyl-1-formyl-(S)-prolineamide | 96 | 30.7 |
| 25 | N-benzyl-1-formyl-(S)-prolineamide | 77 | 23.6 |
| 26 | N-hexyl-1-formyl-(S)-prolineamide | 90 | 20.0 |
| 27 | N-diphenylmethyl-1-formyl-(S)-prolineamide | 91 | 21.0 |
| 28 | N-(1-naphthyl)-1-formyl-(S)-prolineamide | 92 | 42.8 |
| 29 | N-tert-butyl-1-formyl-(S)-prolineamide | 82 | 1.4 |
| 30 | 1-formyl-(S)-prolinebenzyl ester | 90 | 21.4 |
| 31 | 1-formyl-(S)-proline-tert-butyl ester | 88 | 10.8 |
| 32 | 1-formyl-(S)-prolinehexyl ester | 67 | 13.0 |
| 33 | 1-formyl-(S)-prolinephenyl ester | 94 | 9.0 |
| 34 | 1-formyl-1-methylglycylbenzyl ester | 70 | — |

Examples 35 to 43

The operation was conducted in the same manner as in Example 1 but using ketone compounds shown in Table 4 instead of using the acetophenone. The results were as shown in Table 4.

TABLE 4

| Ex. No. | Ketone compound | Product | Yield (%) |
|---|---|---|---|
| 35 | 2-butanone | 2-butanol | 91 |
| 36 | 2-hexanone | 2-hexanol | 90 |
| 37 | 2-octanone | 2-octanol | 88 |
| 38 | cyclohexanone | cyclohexanol | 95 |
| 39 | cyclooctanone | cyclooctanol | 96 |
| 40 | benzophenone | diphenylmethanol | 80 |
| 41 | 2-acetylnaphthalene | 1-(2-naphthyl)-1-ethanol | 86 |

TABLE 4-continued

| Ex. No. | Ketone compound | Product | Yield (%) |
|---|---|---|---|
| 42 | 4-phenylcyclohexanone | 4-phenyl-1-cyclohexanol | 94 |
| 43 | 4-phenyl-2-butanone | 4-phenyl-2-butanol | 85 |

Example 44

Into a 30-ml eggplant-type flask, there were added 0.154 g (1 mmol) of a 4-tert-buylcyclohexanone as a ketone compound, 0.0099 g (0.1 mmols) of a 1-formylpyrrolidine as a formylated product of a cyclic amine, and 5 ml of a methylene chloride as a solvent, which were, then, cooled down to 0° C. in a nitrogen atmosphere. Into the solution was dropwisely added a methylene chloride solution containing 0.203 g (1.5 mmols) of a trichlorosilane to conduct the reaction at room temperature for 24 hours.

After the reaction, the operation was conducted in the same manner as in Example 1 to obtain 0.139 g of a 4-tert-butylcyclohexanol (yield, 89%). The ratio of the cis-modification and the trans-modification of the obtained alcohol compound was 18:82.

Example 45

The operation was conducted in the same manner as in Example 1 but using a 2-methylcyclohexanone instead of using the 4-tert-butylcyclohexanol.

As a result, there was obtained 0.100 g of a 2-methylcyclohexanol (yield 89%). The ratio of the cis-modification and the trans-modification of the obtained alcohol compound was 93:7.

Comparative Example 1

The operation was conducted in the same manner as in Example 1 but using an N,N-dimethylformamide which did not belong to the formamide compound instead of using the 1-formylpyrrolidine. As a result, there was obtained a 1-phenyl-1-ethanol in an amount as small as 0.065 g (yield, 53%).

The formylated products of cyclic amines and amide compounds having an oxo group on a carbon atom at the β-position of the nitrogen atom were prepared by a method described below.

That is, a formylated product of a cyclic amine without substituent on the ring was prepared by reacting a methyl formate with a cyclic amine, or by reacting a cyclic amine with a mixed acid anhydride of a formic acid and an acetic anhydride. The prolineamide derivative was prepared in a manner of reacting an N-t-butoxycarbonyl-proline (N-BOC-proline) with predetermined amines in the presence of a dehydrating agent such as a dicyclohexylcarbodiimide (DCC), removing BOC with a trifluoroacetic acid, or reacting it with a thionyl chloride to prepare an acid chloride which was then reacted with a predetermined amine to transform it into a prolineamide derivative followed by the reaction with a methyl formate.

The proline ester derivative was prepared in a manner of reacting the N-BOC-proline with predetermined amines in the presence of a dehydrating agent such as DCC, removing BOC with the trifluoroacetic acid, or reacting the acid chloride with predetermined alcohol to transform it into a proline ester derivative followed by the reaction with the methyl formate.

The prolinol derivative was prepared in a manner of transforming the proline ester derivative into a prolinol derivative with the sodium borohydride, followed by the reaction with the methyl formate. As required, the prolinol derivative was etherified for its hydroxyl group with the benzyl chloride. Further, the prolinol derivative was prepared by reacting the proline ester derivative with an excess of a phenylmagnesium bromide.

Further, the N-formyl-N-methylglycine ester was synthesized by esterifying the N-methylglycine by the same method as the one described above, followed by the formylation with the methyl formate.

The oxazoline compound was prepared by transforming an amino acid into an amino alcohol with a reducing agent such as lithium aluminum hydride, reacting it with a 37% formaline aqueous solution to form an oxazoline ring, and reacting the resulting compound with a mixed acid anhydride of a formic acid and an acetic anhydride.

Further, the peptide compound was prepared by reacting an N-formylamino acid with an amino acid alkyl ester in the presence of a dehydrating agent such as DCC.

Example 46

54 Milligrams (0.4 mmols) of a trichlorosilane (manufactured by Shin-etsu Kagaku Co.) and 40 mg (0.4 mmols) of a 1-formylpyrrolidine were dissolved in 2 ml of a dichloromethane in a 10-ml eggplant-type flask in a nitrogen atmosphere. One milliliter of the solution was introduced into a sampling tube (5 mm in diameter and 8 inch long, manufactured by Wilmad Co.) and was measured by $^{29}$NMR at 79.4 MHz. As a result, signals were detected at −41.5 ppm and −185.4 ppm, from which it was learned that the trichlorisilane had been transformed into a mixture of a complex having five coordinations and a complex having six coordinations.

Examples 47 to 49

The operation was conducted in the same manner as in Example 46 but using ligands shown in Table 5 instead of using the 1-formylpyrrolidine. The results were as shown in Table 5, from which it was confirmed that the silicon complex having five coordinations existed in the solution no matter which ligand was used.

TABLE 5

| Ex. No. | Ligand compound | NMR signal (ppm) | |
|---|---|---|---|
| 47 | N-phenyl-1-formyl-(S)-prolineamide | −9.4, | −18.8 |
| 48 | N-(1-naphthyl)-1-formyl-(S)-prolineamide | −9.4,<br>−169.5 | −18.6, |
| 49 | 1-formyl-(S)-2-hydroxymethylpyrrolidine | −36.7,<br>−54.1, | −53.1<br>−160.4 |
| 49 | 1-formyl-2-diphenylhydroxymethylpyrrolidine | −9.4, | −18.8 |

Example 50

Into a 30-ml eggplant-type flask, there were added 0.120 g (1 mmol) of an acetophenone (reagent of the special grade manufactured by Wako Junyaku Co.) as a ketone compound and 3 ml of a methylene chloride, which were, then, cooled down to 0° C. in a nitrogen atmosphere. Into the solution was dropwisely added a solution obtained by adding, to 2 ml of a methylene chloride, 0.203 g (1.5 mmols) of a trichlorosilane (manufactured by Shin-etsu Kagaku Co.) and 0.150 g (1.5 mmols) of a 1-formylpyrrolidine in a cooled condition to conduct the reaction at room temperature for 12 hours.

After the reaction, the reaction solution was poured into 15 ml of a mixture solution of methanol and water at a ratio of 1:2, and the extraction operation was effected three times with 30 ml of the methylene chloride. The obtained solution of methylene chloride was dried on magnesium sulfate, condensed, and the residue was isolated and refined through a silica gel column chromatography to obtain 0.112 g of a 1-phenyl-1-ethanol (yield, 92%).

Examples 51 to 54

The operation was conducted in the same manner as in Example 50 but using the formamide compounds shown in Table 6 instead of using the 1-formylpyrrolidine. The results were as shown in Table 6.

TABLE 6

| Ex. No. | Formylamide compound | Yield (%) | Optical Purity R (% ee) |
|---|---|---|---|
| 51 | N-phenyl-1-formyl-(S)-prolineamide | 98 | 32.5 |
| 52 | N-(1-naphthyl)-1-formyl-(S)-prolineamide | 94 | 44.4 |
| 53 | 1-formyl-(S)-2-hydroxymethylpyrrolidine | 96 | 8.8 |
| 54 | 3-formyl-4-(S)-phenylaminocarbonyloxazoline | 85 | 10.0 |

Example 55

Into a 30-ml eggplant-type flask, there were added 0.120 g (1 mmol) of an acetophenone, 0.150 g (1.5 mmols) of a 1-formylpyrrolidine and 5 ml of a methylene chloride, which were, then, cooled down to 0° C. in a nitrogen atmosphere. Into the solution was dropwisely added a methylene chloride solution containing 0.203 g (1.5 mmols) of a trichlorosilane to conduct the reaction for 12 hours.

After the reaction, the after-treatment operation was conducted in the same manner as in Example 5 to obtain 0.110 g of a 1-phenyl-1-ethanol (yield, 90%).

Examples 56 to 58

The operation was conducted in the same manner as in Example 55 but using the formamide compounds shown in Table 7 instead of using the 1-formylpyrrolidine and effecting the reaction for 15 hours. The results were as shown in Table 7.

TABLE 7

| Ex. No. | Formylamide compound | Yield (%) | Optical Purity R (% ee) |
|---|---|---|---|
| 56 | N-phenyl-1-formyl-(S)-prolineamide | 99 | 32.5 |
| 57 | N-(1-naphthyl)-1-formyl-(S)-prolineamide | 95 | 44.0 |
| 58 | 1-formyl(S)-2-hydroxymethylpyrrolidine | 98 | 8.7 |

Example 59

The operation was conducted in the same manner as in Example 55 but using the 1-formylpyrrolidine in an amount of 0.1 mmol and conducting the reaction for 24 hours to obtain 0.068 g of a 1-phenyl-1-ethanol (yield, 56%).

Examples 60 to 63

The operation was conducted in the same manner as in Example 55 but using formamide compounds shown in Table 8 in an amount of 0.1 mmol and conducting the reaction for 24 hours. The results were as shown in Table 8.

TABLE 8

| Ex. No. | Formylamide compound | Yield (%) | Optical Purity R (% ee) |
|---|---|---|---|
| 60 | N-phenyl-1-formyl-(S)-prolineamide | 96 | 30.7 |
| 61 | N-(1-naphthyl)-1-formyl-(S)-prolineamide | 92 | 42.8 |
| 62 | 1-formyl(S)-2-hydroxymethylpyrrolidine | 61 | 6.4 |
| 63 | 3-formyl-4-(S)-phenylaminocarbonyloxazoline | 40 | 10.2 |

Example 64

The operation was conducted in the same manner as in Example 59 but using an N-formyl-L-prolyl-D-phenylalanylmethyl ester instead of using the 1-formylpyrrolidine to obtain 0.085 g of a 1-phenyl-1-ethanol (yield, 70%). The optical purity thereof was 25% ee, and the main product was an R-modification.

Examples 65 to 73

The operation was conducted in the same manner as in Example 55 but using ketone compounds shown in Table 9 instead of using the acetophenone. The results were as shown in Table 9.

TABLE 9

| Ex. No. | Ketone compound | Product | Yield (%) |
|---|---|---|---|
| 65 | 2-butanone | 2-butanol | 91 |
| 66 | 2-hexanone | 2-hexanol | 90 |
| 67 | 2-octanone | 2-octanol | 88 |
| 68 | cyclohexanone | cyclohexanol | 95 |
| 69 | cyclooctanone | cyclooctanol | 96 |
| 70 | benzophenone | diphenylmethanol | 80 |
| 71 | 2-acetylnaphthalene | 1-(2-naphthyl)-1-ethanol | 86 |
| 72 | 4-phenylcyclohexanone | 4-phenyl-1-cyclohexanol | 94 |
| 73 | 4-phenyl-2-butanone | 4-phenyl-2-butanol | 85 |

Comparative Example 2

The operation was conducted in the same manner as in Example 46 but using an N,N-dimethylformamide which did not belong to the formamide compound instead of using the 1-formylpyrrolidine. As a result, signals were observed at −186.4 ppm and at −192.0 ppm, and the complex possessed six coordinations.

Comparative Example 3

The operation was conducted in the same manner as in Example 55 but using an N,N-dimethylformamide instead of using the 1-formylpyrrolidine. As a result, there was obtained a 1-phenyl-1-ethanol in an amount as small as 0.064 g (yield, 53%).

Comparative Example 4

The operation was conducted in the same manner as in Example 59 but using an N,N-dimethylformamide instead of using the 1-formylpyrrolidine. As a result, there was obtained a 1-phenyl-1-ethanol in an amount as small as 0.034 g (yield, 28%).

Example 74

Into a 30-ml eggplant-type flask, there were added 0.192 g (2 mmols) of a 2-cyclohexene-1-on, 0.020 g (0.2 mmols)

of a 1-formylpyrrolidine and 10 ml of a methylene chloride as a solvent, which were, then, cooled down to 0° C. in a nitrogen atmosphere. Into the solution was dropwisely added 3 ml of a methylene chloride solution containing 0.813 g (6 mmols) of a trichlorosilane to conduct the reaction at room temperature for 45 hours.

After the reaction, the operation was conducted in the same manner as in Example 50 to obtain 0.175 g of a cyclohexanol (yield, 87%) and 0.021 g of a 2-cyclohexene-1-ol (yield, 11%).

Example 75

Into a 30-ml eggplant-type flask, there were added 0.195 g (1 mmol) of a 1-phenylimino-1-phenylethane, 0.022 g (0.1 mmol) of a 1-formyl-L-prolinephenylamide and 4 ml of a methylene chloride as a solvent, which were, then, cooled down to 0° C. in a nitrogen atmosphere. Into the solution was dropwisely added 2 ml of a methylene chloride solution containing 0.203 g (1.5 mmols) of a trichlorosilane to conduct the reaction at room temperature for 24 hours.

After the reaction, the operation was conducted in the same manner as in Example 50 to obtain 0.180 g of an N-phenyl-1-phenylethylamine (yield, 91%). The optical purity thereof was 55%ee, and the main product was of an R-modification.

Example 76

The operation was conducted in the same manner as in Example 75 but changing the ligand into a 1-formyl-L-proline(1-naphthyl)amide. As a result, where was obtained 0.103 g of an N-phenyl-1-phenylethylamine (yield, 52%). The optical purity thereof was 66% ee, and the main product was of an R-modification.

Examples 77 to 79

The operation was conducted in the same manner as in Example 76 but using compounds shown in Table 10 instead of using the imine compound. The results were as shown in Table 10.

TABLE 10

| Ex. No. | Imine compound | Product | Yield (%) | Optical purity % ee R |
|---|---|---|---|---|
| 77 | 1-benzylimino-1-phenylethane | N-bezyl-1-phenylethylamine | 97 | 55 |
| 78 | 1-phenylimino-1-phenylethane | N-phenyl-1-phenylethylamine | 52 | 66 |
| 79 | 1-phenylimino-1-(4-nitrophenyl) ethane | N-phenyl-1-(4-nitrophenyl) ethylamine | 99 | 49 |

Example 80

Into a 30-ml eggplant-type flask, there were added 0.212 g (2 mmols) of a benzaldehyde, 2.0 mg (0.02 mmols) of a 1-formylpyrrolidine and 10 ml of a methylene chloride as a solvent, which were, then, cooled down to 0° C. in a nitrogen atmosphere. Into the solution was dropwisely added 2 ml of a methylene chloride solution containing 0.406 g (3 mmols) of a trichlorosilane to conduct the reaction at 0° C. for 5 hours.

After the reaction, the operation was conducted in the same manner as in Example 50 to obtain 0.210 g of a benzyl alcohol (yield, 97%).

Examples 81 to 85

The operation was conducted in the same manner as in Example 80 but using, as starting materials, aldehyde compounds shown in Table 11 instead of using the benzaldehyde. The results were as shown in Table 11.

TABLE 11

| Ex. No. | Aldehyde compound | Product | Yield (%) |
|---|---|---|---|
| 81 | 4-chlorobenzaldehyde | 4-chlorobenzyl alcohol | 96 |
| 82 | 4-nitrobenzaldehyde | 4-nitrobenzyl alcohol | 95 |
| 83 | 2-furaldehyde | 2-furfuryl alcohol | 98 |
| 84 | hexanal | hexanol | 75 |
| 85 | octanal | octanol | 79 |

Comparative Example 5

The operation was conducted in the same manner as in Example 80 but using an N,N-dimethylformamide instead of using the 1-formylpyrrolidine. As a result, there was obtained a benzyl alcohol in an amount as small as 0.054 g (yield, 25%).

Example 86

Into a 30-ml eggplant-type flask, there were added 0.362 g (2 mmols) of an N-benzylidenealanine, 2.0 mg (0.02 mmols) of a 1-formylpyrrolidine and 4 ml of a methylene chloride as a solvent, which were, then, cooled down to 0° C. in a nitrogen atmosphere. Into the solution was dropwisely added 2 ml of a methylene chloride solution containing 0.406 g (3 mmols) of a trichlorosilane to conduct the reaction at 0° C. for 3 hours.

After the reaction, the operation was conducted in the same manner as in Example 50 to obtain 0.352 g of an N-benzylalanine (yield, 96%).

Examples 87 to 90

The operation was conducted in the same manner as in Example 86 but using, as starting materials, imine compounds shown in Table 12 instead of using the N-benzylidenealanine. The results were as shown in Table 12.

TABLE 12

| Ex. No. | Imine compound | Product | Yield (%) |
|---|---|---|---|
| 87 | N-benzylideneamine | N-benzylamine | 96 |
| 88 | N-bezylidenemethylamine | N-methylbenzylamine | 97 |
| 89 | 1-methylimino-1-phenylethane | N-methyl-1-phenylethylamine | 88 |
| 90 | N-hexylidenemethylamine | cyclohexylmethylamine | 80 |

Comparative Example 6

The operation was conducted in the same manner as in Example 86 but using an N,N-dimethylformamide instead of using the 1-formylpyrrolidine. As a result, there was obtained an N-benzylalanine in an amount of as small as 0.183 g (yield, 50%).

What is claimed is:

1. A method of preparing a reduced product of an unsaturated organic compound by mixing the unsaturated organic compound and a trichlorosilane together to reduce the unsaturated organic compound in the presence of a ligand compound which, when mixed together with the trichlorosilane, gives a signal at −15 to −120 ppm as measured by $^{29}$Si-NMR at 74.9 MHz.

2. A method of preparing a reduced product of an unsaturated organic compound according to claim 1, wherein said ligand compound is the one capable of giving a signal at −15 to −120 ppm as measured by $^{29}$Si-NMR at 74.9 MHz in a solution obtained by adding, into a solution of 0.2 mols of the trichlorosilane/liter, the ligand compound in an equimolar amount to the trichlorosilane.

3. A method of preparing a reduced product of an unsaturated organic compound according to claim 1, wherein said ligand compound is an N-formylated product of a secondary amine having not less than 3 carbon atoms.

4. A method of preparing a reduced product of an unsaturated organic compound according to claim 3, wherein said secondary amine having not less than 3 carbon atoms is a cyclic amine having not less than 3 carbon atoms or a secondary amine in which a carbon atom at the β-position of a nitrogen atom has an oxo group.

5. A method of preparing a reduced product of an unsaturated organic compound according to claim 1, wherein said unsaturated organic compound is at least the one selected from the group consisting of a ketone compound, an aldehyde compound and an imine compound.

6. A method of preparing a reduced product of an unsaturated organic compound according to claim 5, wherein said unsaturated organic compound is a ketone compound.

7. A method of preparing a reduced product of an unsaturated organic compound according to claim 5, wherein said unsaturated organic compound is an aldehyde compound.

8. A method of preparing a reduced product of an unsaturated organic compound according to claim 5, wherein said unsaturated organic compound is an imine compound.

9. A reducing agent comprising:
(a) a mononuclear silicon complex in which a silicon atom has a coordination number of 5, and among the five ligands coordinated on the silicon atom in the silicon complex, four ligands include a hydrogen atom and three chlorine atoms, and the remaining one ligand is a ligand compound capable of forming a stable silicon complex having five coordinations upon acting on the trichlorosilane and/or,
(b) a binuclear silicon complex in which each silicon atom has a coordination number of 6, and among the six ligands coordinated on each silicon atom in the silicon complex, five ligands include a hydrogen atom and four chlorine atoms, and the remaining one ligand acts upon the trichlorosiline to form a stable silicon complex having five coordinations.

10. A reducing agent according to claim 9, wherein the ligand compound capable of forming a stable silicon complex having five coordinations upon acting on the trichlorosilane is the one capable of forming a silicon complex having five coordinations that can be detected when a solution is measured by $^{29}$Si-NMR at 74.9 MHz, the solution being obtained by having the ligand compound acted on the trichlorosilane in an equimolar amount thereto in a solution of 0.2 mols of the trichlorosilane/liter.

11. A reducing agent according to claim 9, wherein the ligand compound capable of forming a stable silicon complex having five coordinations upon acting on the trichlorosilane is the one that gives a signal at −15 to −120 ppm when a solution is measured by $^{29}$Si-NMR at 74.9 MHz, the solution being obtained by adding, to a solution of 0.2 mols of the trichlorosilane/liter, the ligand compound in an equimolar amount to the trichlorosilane.

12. A reducing agent according to claim 9, wherein the ligand compound capable of forming a stable silicon complex having five coordinations upon acting on the trichlorosilane is an N-formyl compound of a secondary amine having not less than 3 carbon atoms.

13. A reducing agent according to claim 12, wherein the secondary amine having not less than 3 carbon atoms is a cyclic amine with not less than 3 carbon atoms or a secondary amine in which a carbon atom at the β-position of a nitrogen atom has an oxo group.

14. A reducing agent comprising a silicon complex obtained by mixing a trichlorosilane and a ligand compound which, when mixed together with the trichlorosilane, gives a signal at −15 to −120 ppm as measured by 29Si-NMR at 74.9 MHz.

15. A reducing agent according to claim 14, wherein said ligand compound is the one capable of giving a signal at −15 to −120 ppm as measured by $^{29}$Si-NMR at 74.9 MHz in a solution obtained by adding, into a solution of 0.2 mols of the trichlorosilane/liter, the ligand compound in an equimolar amount to the trichlorosilane.

* * * * *